United States Patent
Li et al.

(10) Patent No.: US 6,962,817 B2
(45) Date of Patent: Nov. 8, 2005

(54) REFERENCE CONTROL FOR OPTICAL MEASUREMENT OF NUCLEATED RED BLOOD CELLS OF A BLOOD SAMPLE

(75) Inventors: Yi Li, Miami, FL (US); Nery Ortiz, Miami, FL (US); Carole J. Young, Raleigh, NC (US); Santiago Galvez, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 10/955,104

(22) Filed: Sep. 30, 2004

(65) Prior Publication Data

US 2005/0074894 A1 Apr. 7, 2005

Related U.S. Application Data

(60) Provisional application No. 60/508,161, filed on Oct. 2, 2003.

(51) Int. Cl.$^7$ .............................................. G01N 33/48
(52) U.S. Cl. ............................. 436/63; 436/8; 436/10; 436/164; 435/2
(58) Field of Search .............................. 436/8, 10, 63, 436/164, 16; 435/2; 252/408.1

(56) References Cited

U.S. PATENT DOCUMENTS

| | | | | |
|---|---|---|---|---|
| 4,331,862 A | * | 5/1982 | Ryan ............................ | 377/29 |
| 4,704,364 A | | 11/1987 | Carver et al. | |
| 4,704,891 A | * | 11/1987 | Recktenwald et al. ... | 250/252.1 |
| 4,767,206 A | * | 8/1988 | Schwartz ...................... | 356/73 |
| 5,320,964 A | | 6/1994 | Young et al. | |
| 5,512,485 A | | 4/1996 | Young et al. | |
| 5,559,037 A | | 9/1996 | Kim et al. | |
| 5,648,225 A | | 7/1997 | Kim et al. | |
| 5,858,790 A | | 1/1999 | Kim et al. | |
| 5,874,310 A | * | 2/1999 | Li et al. ........................ | 436/10 |
| 5,879,900 A | | 3/1999 | Kim et al. | |
| 5,917,584 A | | 6/1999 | Li et al. | |
| 6,074,879 A | * | 6/2000 | Zelmanovic et al. ......... | 436/10 |
| 6,187,590 B1 | | 2/2001 | Kim et al. | |
| 6,200,500 B1 | * | 3/2001 | Ryan ........................ | 252/408.1 |
| 6,221,668 B1 | | 4/2001 | Ryan et al. | |
| 6,350,619 B1 | * | 2/2002 | Mercolino et al. .......... | 436/518 |
| 6,399,388 B1 | | 6/2002 | Ryan et al. | |
| 6,403,377 B1 | | 6/2002 | Ryan et al. | |
| 6,406,915 B2 | | 6/2002 | Ryan et al. | |
| 6,448,085 B1 | * | 9/2002 | Wang et al. .................. | 436/10 |
| 6,514,763 B2 | | 2/2003 | Carver et al. | |
| 6,521,729 B1 | | 2/2003 | Zelmanovic et al. | |
| 6,573,102 B2 | | 6/2003 | Li et al. | |
| 6,653,063 B2 | | 11/2003 | Carver et al. | |
| 6,653,137 B2 | | 11/2003 | Ryan | |
| 6,723,563 B2 | | 4/2004 | Ryan | |
| 2001/0046708 A1 | | 11/2001 | Carver et al. | |

\* cited by examiner

*Primary Examiner*—Maureen M. Wallenhorst
(74) *Attorney, Agent, or Firm*—Cuspa Technology Law Associates; Mitchell E. Alter

(57) ABSTRACT

Reference control compositions and the method of use are disclosed for measurement of nucleated red blood cells, which includes one set of synthetic spherical particles having a mean particle diameter ranging from 6.2 μm to 6.8 μm and a refractive index from 1.58 to 1.62 monodispersed in an aqueous suspension medium. The synthetic spherical particles have optical properties simulating optical properties of nucleated red blood cells as measured by optical measurements. The reference control composition can further include a second set of the synthetic spherical particles having optical properties simulating optical properties of white blood cells. Further disclosed is a reference control system which includes a series of reference control compositions, each having an amount of one type of synthetic spherical particles which have optical properties simulating the optical properties of nucleated red blood cells having a specific cell maturity.

30 Claims, 6 Drawing Sheets

REFERENCE CONTROL FOR OPTICAL MEASUREMENT OF NUCLEATED RED BLOOD CELLS OF A BLOOD SAMPLE

CROSS REFERENCE TO RELATED APPLICATION

This application claims the benefit under 35 USC 119 (e) of the provisional patent application Ser. No. 60/508,161, filed on Oct. 2, 2003, which is herein incorporated by reference in its entirety.

FIELD OF THE INVENTION

The present invention relates to a reference control composition for determination of nucleated blood cells of a blood sample. More specifically, the reference control composition comprises synthetic spherical particles having optical properties simulating nucleated red blood cells as measured by optical measurements.

BACKGROUND OF THE INVENTION

Flow cytometric instruments generally rely on optical signals for the analysis of particles which pass through a focused flow cell. Usually, calibration and/or analysis of a reference control product to confirm instrument operating conditions are required prior to performing a particle analysis, in order to ensure accurate and reliable assay results.

Quality control has long been a necessary and routine procedure in clinical hematology. Accuracy in the counting of various types of blood cells is dependent, in part, upon the use of adequate control products and methods of using the control products. With the numerous types of equipment for particle counting now available, quality control by the use of control products is necessary, since the possibility of instrument malfunctioning is ever present. The traditional method of maintaining a quality control program for automatic particle counting equipment has consisted of providing fresh human blood as a whole blood standard. However, this fresh blood is usable for only one day, therefore, various manufactured control products which have longer product lifetime have been developed.

Commonly used particles in a control product simulate or approximate the types of particles or cells that are intended to undergo analysis. Consequently, these particles have been frequently referred to as analog particles. The analog particles should be selected or made so that they have certain characteristics that are similar to those of the particles or cells to be analyzed in the instruments. Exemplary characteristics and parameters include similarities in size, volume, surface characteristics, granularity properties, light scattering properties and fluorescence properties.

Various commercial reference control products are now available, which use various processed or fixed human or animal blood cells as analogs of human blood cells. U.S. Pat. No. 5,512,485 (to Young, et al) teaches a hematology control comprising several white blood cell analogs made of processed and fixed animal red blood cells. U.S. Pat. Nos. 6,187,590 and 5,858,790 (to Kim, et al) teach a hematology control comprising a nucleated red blood cell (NRBC) analog made of lysed and fixed avian or fish red blood cells. U.S. Pat. Nos. 6,406,915, 6,403,377, 6,399,388, 6,221,668, and 6,200,500 (to Ryan, et al) teach a hematology control comprising a NRBC analog derived from avian blood cells. U.S. Pat. No. 6,448,085 (to Wang, et al) teaches a hematology control comprising a nucleated red blood cell (NRBC) analog derived from chicken blood and fixed human blood with nucleated red blood cells. This prior art teaches measurement of cell size and fluorescent intensity of the control material to facilitate a determination of nucleated red blood cell staging. U.S. Pat. Nos. 6,653,137 and 6,723,563 (to Ryan) teach methods of making and using a hematology reference control which contains a nucleated red blood cell component made by lysing and removing cytoplasm from reptile or fish blood cells.

In addition to the use of blood cell analogs for control purposes, synthetic microspheres have also been used in flow cytometry control products. More specifically, U.S. Pat. No. 6,074,879 (to Zelmanovic, et al) teaches a method using synthetic spherical particles for calibrating and standardizing a flow cytometric instrument for particle analysis. The prior art specifically teaches using particles having average mean particle diameters and refractive index essentially reproducible of the particles or cells to be assayed. U.S. Pat. No. 6,521,729 (to Zelmanovic, et al) further teaches a hematology calibration and reference control which comprises fluorine-containing spherical particles having an average mean particle diameter of about 5 to 5.5 $\mu$m and a refractive index of about 1.4.

On the other hand, several detection methods for measuring nucleated red blood cells in a blood sample on a flow cytometric instruments have been reported. U.S. Pat. No. 5,879,900 (to Kim, et al) teaches a method of differentiating nucleated red blood cells by measuring two low angles of light scatter and a fluorescence signal of a blood sample under lysing condition. U.S. Pat. Nos. 5,874,310 and 5,917,584 (to Li, et al) teach a method of differentiating nucleated red blood cells by measuring two angles of light scatter signals of a blood sample under lysing condition.

Currently, reference controls for nucleated red blood cells taught by prior art are limited to the use of stabilized, processed or fixed blood cells as the nucleated red blood cell analog particles. It is known that processes for manufacturing these blood cells for a control product are complex and costly, and the analog particles have limited stability and are prone to lot-to-lot variation.

Therefore, it is desirable to use synthetic particles as nucleated red blood cell analog in a reference control composition, wherein the synthetic particles simulate the properties of nucleated red blood cell population under specific reaction and detection conditions.

SUMMARY OF THE INVENTION

In one embodiment, the present invention is directed to a reference control composition for measurement of nucleated blood cells comprising an amount of one type of synthetic spherical particles having a mean particle diameter ranging from about 6.2 $\mu$m to about 6.8 $\mu$m and a refractive index from about 1.58 to about 1.62 monodispersed in an aqueous suspension medium. The synthetic spherical particles have optical properties simulating optical properties of nucleated red blood cells as measured by optical measurements. More specifically, the synthetic spherical particles are polystyrene particles having a refractive index about 1.59. The optical measurements are a low angle light scatter measurement and an axial light loss measurement, or two low angle light scatter measurements.

The reference control composition can further comprise a white blood cell component, a red blood cell component, a platelet component, and a reticulocyte component.

In a further embodiment, the present invention is directed to a reference control system for measurement of nucleated blood cells. The reference control system comprises a series of reference control compositions, each thereof comprising an amount of one type of synthetic spherical particles having a mean particle diameter ranging from about 6.2 μm to about 6.8 μm and a refractive index from about 1.58 to about 1.62 monodispersed in an aqueous suspension medium. Each type of synthetic spherical particles has optical properties which simulate optical properties of nucleated red blood cells having a specific cell maturity.

In another embodiment, the present invention is directed to a reference control composition which comprises two sets of synthetic spherical particles having a mean particle diameter ranging from about 6 μm to about 12 μm and a refractive index from about 1.58 to about 1.62 monodispersed in an aqueous suspension medium. The first set of synthetic spherical particles has optical properties simulating optical properties of nucleated red blood cells as measured by optical measurements. The second set of synthetic spherical particles has optical properties simulating optical properties of white blood cells under the same condition. The first set of synthetic spherical particles is polystyrene particles having a refractive index about 1.59, and the second set of synthetic spherical particles can be polystyrene particles or carboxylated polystyrene particles.

In yet a further embodiment, the reference control composition can include two sets of synthetic spherical particles which have optical properties simulating optical properties of at least two white blood cell subpopulations. This reference control composition can be used for the measurement of nucleated red blood cells and differentiation of white blood cell subpopulations.

In a further aspect, the present invention is directed to a method of using the reference control composition for measurement of nucleated blood cells. The method comprises the steps of: providing the reference control composition to a flow cytometric instrument capable of measuring nucleated red blood cells by optical measurements, the reference control composition comprising an amount of one type of synthetic spherical particles having a mean particle diameter ranging from about 6.2 μm to about 6.8 μm and a refractive index from about 1.58 to about 1.62 monodispersed in an aqueous suspension medium; wherein the synthetic spherical particles have optical properties simulating optical properties of nucleated red blood cells as measured by the optical measurements; analyzing the reference control composition in a focused flow cell by the optical measurements; and reporting numbers of nucleated red blood cells of the reference control composition.

Moreover, the reference control composition can further comprise a white blood cell component, a red blood cell component, a platelet component, and a reticulocyte component; and the method can further comprise analyzing and reporting white blood cells, red blood cells, platelets, and reticulocytes.

In another embodiment, the method comprises providing a reference control composition comprising multiple sets of synthetic spherical particles having a mean particle diameter ranging from about 6 μm to about 12 μm and a refractive index from about 1.58 to about 1.62 monodispersed in an aqueous suspension medium, wherein the first set of the synthetic spherical particles has optical properties simulating optical properties of nucleated red blood cells as measured by the optical measurements, and the second set of the synthetic spherical particles has optical properties simulating optical properties of white blood cell; analyzing the reference control composition in a focused flow cell by the optical measurements; and differentiating the first and the second sets of the synthetic spherical particles, and reporting numbers of nucleated red blood cells and numbers of white blood cells of the reference control composition.

DETAILED DESCRIPTION OF THE INVENTION

Figure 1A:
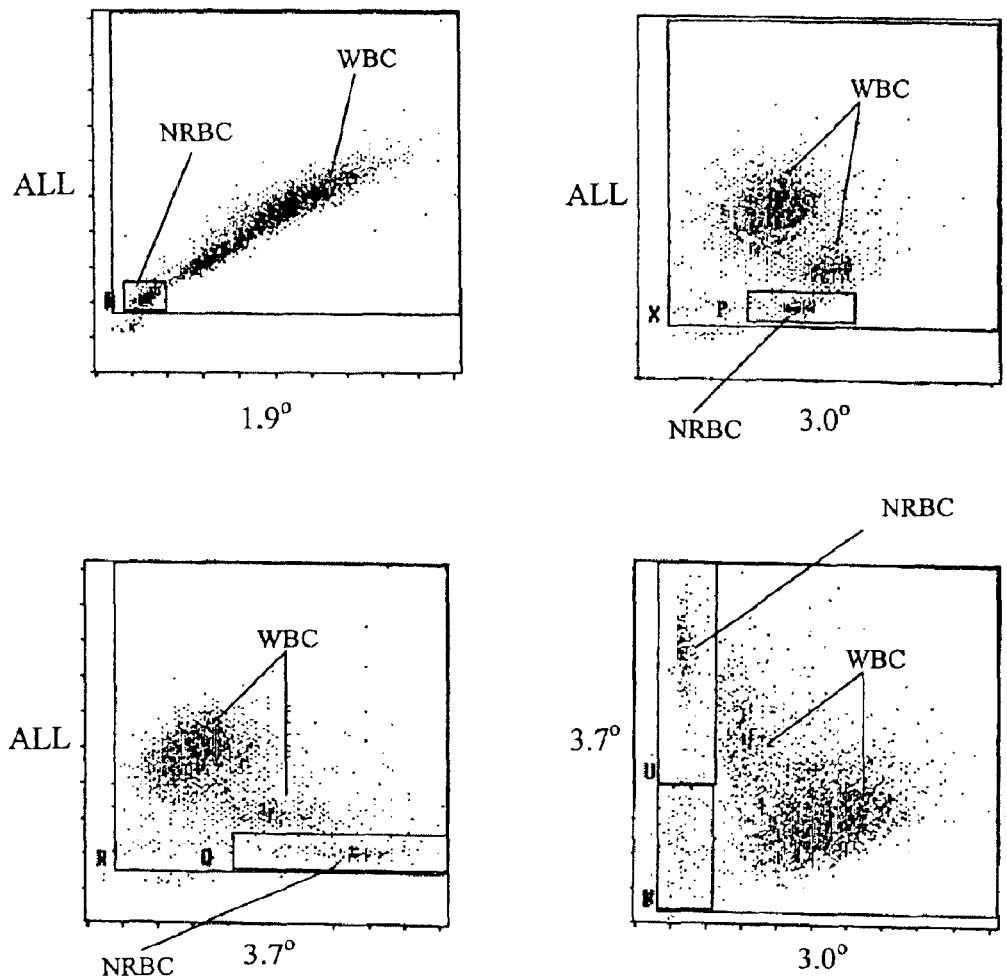
FIG. 1A shows various scattergrams of a clinical whole blood sample which contained about 5 NRBCs per 100 WBC.

In one embodiment, the present invention provides a reference control composition for measuring nucleated red blood cells on a flow cytometric instrument. The reference control composition comprises an amount of one type of synthetic spherical particles having a mean particle diameter ranging from about 6.2 μm to about 6.8 μm and a refractive index from about 1.58 to about 1.62, monodispersed in an aqueous suspension medium. The synthetic spherical particles have optical properties that simulate the optical properties of nucleated red blood cells (NRBCs) as measured by optical measurements. The reference control composition can be used as a control for measurement of nucleated red blood cells by the optical measurements. Herein, the phase of "one type of synthetic spherical particles" means that the individual particles are made of a same material and have the same, within the error range, mean particle diameter and refractive index.

In a further embodiment, the reference control composition comprises multiple sets of synthetic spherical particles having a mean particle diameter ranging from about 6 μm to about 12 μm and a refractive index from about 1.58 to about 1.62 monodispersed in an aqueous suspension medium. The first set of synthetic spherical particles has optical properties simulating optical properties of nucleated red blood cells under a blood lysing condition as measured by optical measurements. The second set of synthetic spherical particles has optical properties simulating optical properties of white blood cells under the same condition. Herein, the phase of "a set of synthetic spherical particles" means an amount of one type of synthetic spherical particles, wherein the individual particles are made of a same material and have the same, within the error range, mean diameter and refractive index.

The optical measurements for measuring nucleated red blood cells for the purpose of the present invention can be (a) a low angle light scatter measurement and an axial light loss measurement, or (b) two low angle light scatter measurements. The phrase "low angle light scatter measurement" used herein refers to the measurement of light scatter signals at an angle in less than 10° from the incident light. Axial light loss (ALL, also known as forward extinction) is generally the decrease in light energy due to a particle or a cell passing in front of a laser beam and being detected by a photodiode. The light loss is generally due to scattering and absorption, and is defined as the decrease in light energy reaching a detector in the path of the light beam due to the passage of a particle or a cell through that light beam (generally ALL is detected at an angle of from about 0° to about 1°). In a preferred embodiment, ALL signal is collected in a circular area less than about 0.5° from the incident light axis. ALL is influenced strongly by the particle size.

The instrument used for measuring nucleated red blood cells in a blood sample was a modified Coulter XL™ flow cytometer. The experimental flow cytometric instrument was equipped with an optical detector enabling light scatter measurements at various angles including low angle light scatter, such as 1.9°, 3.0°, 3.7° and axial light loss. The dimension of the aperture of the flow cell can be either 250 $\mu$m or 50 $\mu$m. An isotonic blood diluent and a lysing reagent were used to dilute the blood sample and to lyse the red blood cells.

Example 1 illustrates an example of measuring the nucleated red blood cells under a blood lysing condition by optical measurement using the described experimental flow cytometric instrument. Under the blood lysing condition, the red blood cells are lysed, both white blood cells and nucleated red blood cells are partially lysed, their cell volumes reduce substantially. The size of the nucleated red blood cells reduces down to about their nuclei volume.

Figure 1B:
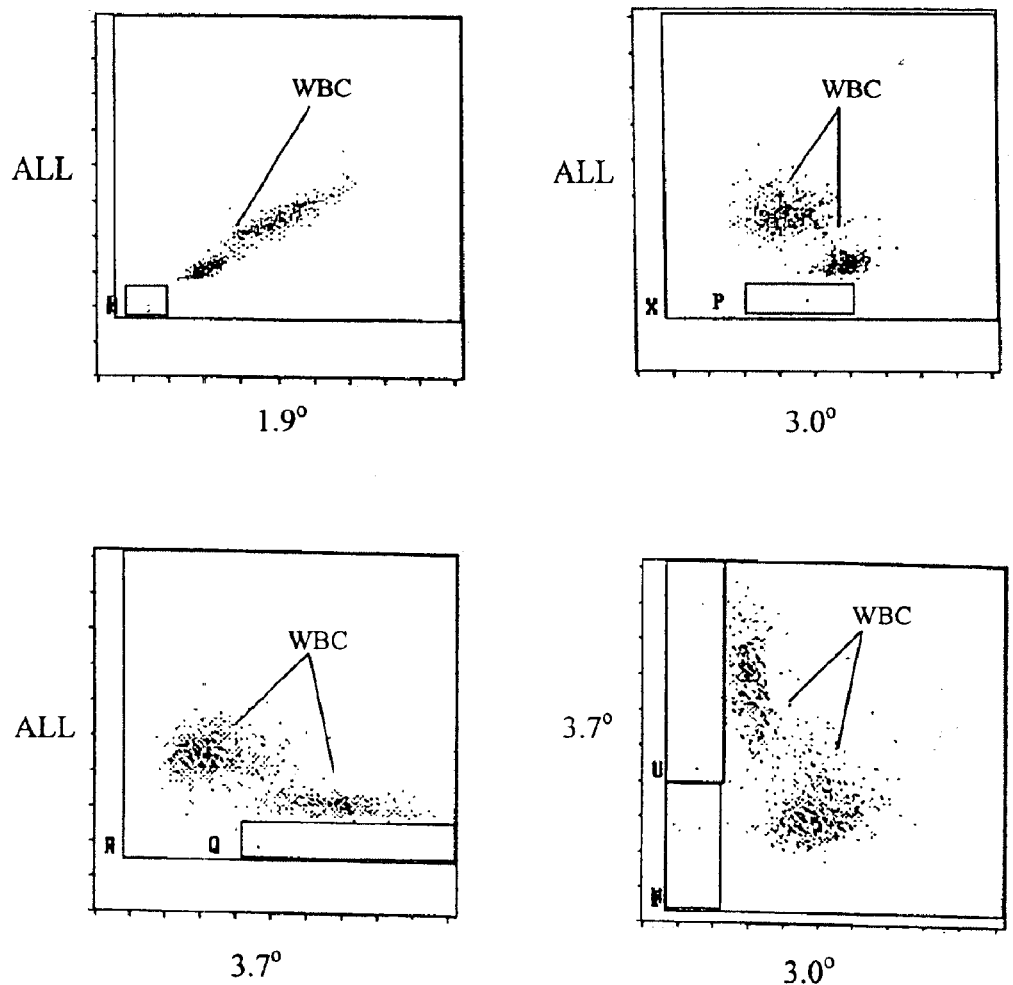
FIG. 1B shows various scattergrams of a normal blood sample.

FIG. 1A shows four scattergrams obtained under the condition described in Example 1 from a clinical whole blood sample which contained about 5 NRBCs per 100 white blood cells. The four scattergrams are ALL vs. 1.9°, ALL vs. 3.0°, ALL vs. 3.7°, and 3.7° vs. 3.0° scattergrams, respectively. As shown, the nucleated red blood cells appeared as a distinct cluster in a specific region of a corresponding scattergram. The specific region in a scattergram is hence referred to as a NRBC region. It is noted that in different scattergrams the NRBC regions can be different. FIG. 1B shows the corresponding scattergrams obtained from a normal whole blood sample. As shown, no cell population appears in the corresponding NRBC regions.

Figure 2:
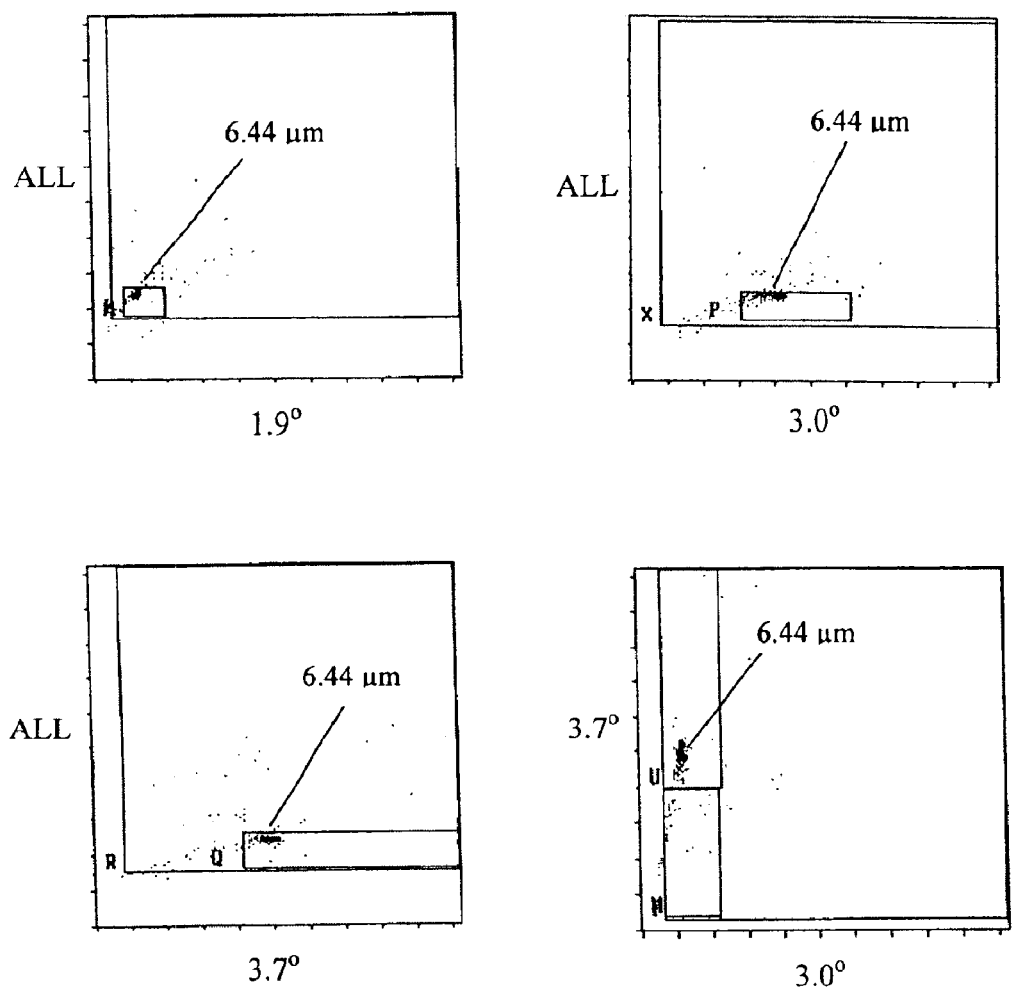
FIG. 2 shows various scattergrams of 6.44 μm polystyrene particles.

In one exemplary embodiment, polystyrene particles having a mean particle diameter of 6.44 $\mu$m and a refractive index of 1.59 were used to simulate optical properties of human nucleated red blood cells under the lysing condition described above. FIG. 2 shows scattergrams of the polystyrene particles obtained under the condition described in Example 2. As shown, 6.44 $\mu$m polystyrene particles located in the NRBC region of human nucleated red blood cells under the condition described above. The synthetic particle simulating optical properties of nucleated red blood cells is hence also referred as NRBC analog hereinafter. It is noted that the specific size of the synthetic particles referred herein is the mean diameter of the particles.

Figure 3:
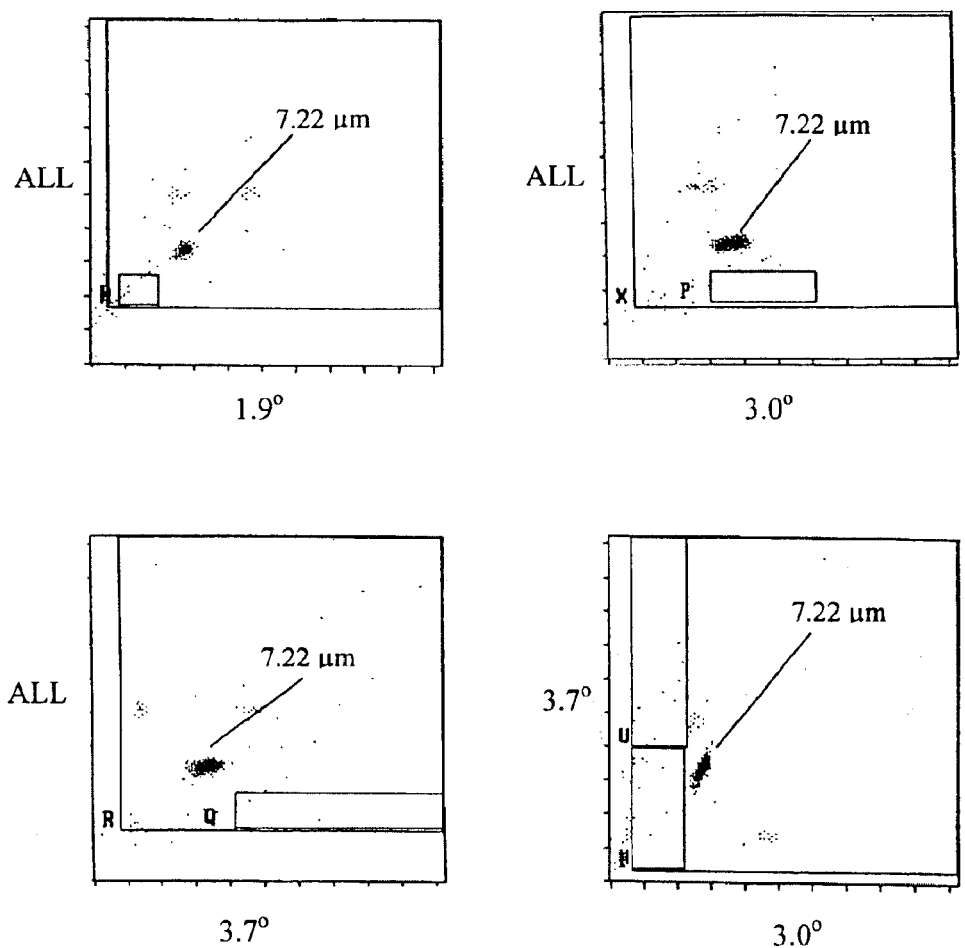
FIG. 3 shows various scattergrams of 7.22 μm polystyrene particles

As another example, polystyrene particles having a mean particle diameter of 6.44 $\mu$m and a refractive index of 1.59 were used to simulate white blood cells (WBC) under the reaction condition and measurements described above. FIG. 3 shows scattergrams of 7.22 $\mu$m polystyrene particles obtained under the condition described in Example 2. As shown, 7.22 $\mu$m polystyrene particles located outside the NRBC regions, but appeared in the same region of human white blood cells under the condition described above.

In a further example, dark blue carboxylated polystyrene particles having a mean diameter of 10.9 $\mu$m and a refractive index of 1.60 were also used to simulate white blood cells under the condition described above.

It should be understood that to simulate optical properties of white blood cells, or in other words to function as a white blood cell analog, the synthetic particles can locate in a large area of the scattergrams so long as the synthetic particles do not overlap with the defined NRBC region. Preferably, the white blood cell analog has similar optical properties of one major white blood cell subpopulations, such as granulocytes or lymphocytes.

In yet a further embodiment, the reference control composition can further comprise two sets of synthetic spherical particles that simulate the optical properties of two different white blood cell subpopulations under the condition, for example, lymphocytes and granulocytes. This reference control composition can be used for simultaneous measurement of nucleated red blood cells and differentiation of white blood cell subpopulations.

Alternatively, the WBC analog can also be made of cellular particles which simulate the optical properties of white blood cells under the lysing condition. Suitable examples of WBC analog made of cellular particles include stabilized mammalian white blood cells, and processed and/or fixed human and animal red blood cells, as known in the art.

In another embodiment, the present invention provides a reference control composition which comprises the above described synthetic spherical particles that simulate optical properties of nucleated red blood cells and white blood cells, and a red blood cell component and a platelet component, dispersed in an aqueous suspension medium.

The red blood cell component can be stabilized mammalian red blood cells, preferably, stabilized human red blood cells. The process of making red blood cell component has been described in details in U.S. Pat. No. 4,704,364, which is herein incorporated by references in its entirety. The platelet component can be stabilized human or animal platelets, or platelet analogs made from other cell types. One suitable example is processed goat red blood cells as the platelet analog, as disclosed in U.S. Pat. No. 4,704,364, which is herein incorporated by references in its entirety.

The red blood cells of a blood sample and the stabilized human red blood cells in the reference control composition are lysed under the lysing condition, and should not be detected in the measurement of nucleated red blood cells and white blood cells. The platelets of a blood sample under the lysing condition reduce substantially in size and they are below the detection threshold for the measurement of nucleated red blood cells. The platelet analog described above simulates platelet response under the lysing condition. Therefore, the presence of red blood cells and platelets in the reference control composition reflect the response of the control composition to the lysing reagent, as well as the reaction conditions on the instrument. Hence, the reference control composition containing red blood cell and platelet components can provide further information related to the instrument operating conditions.

Figure 4:
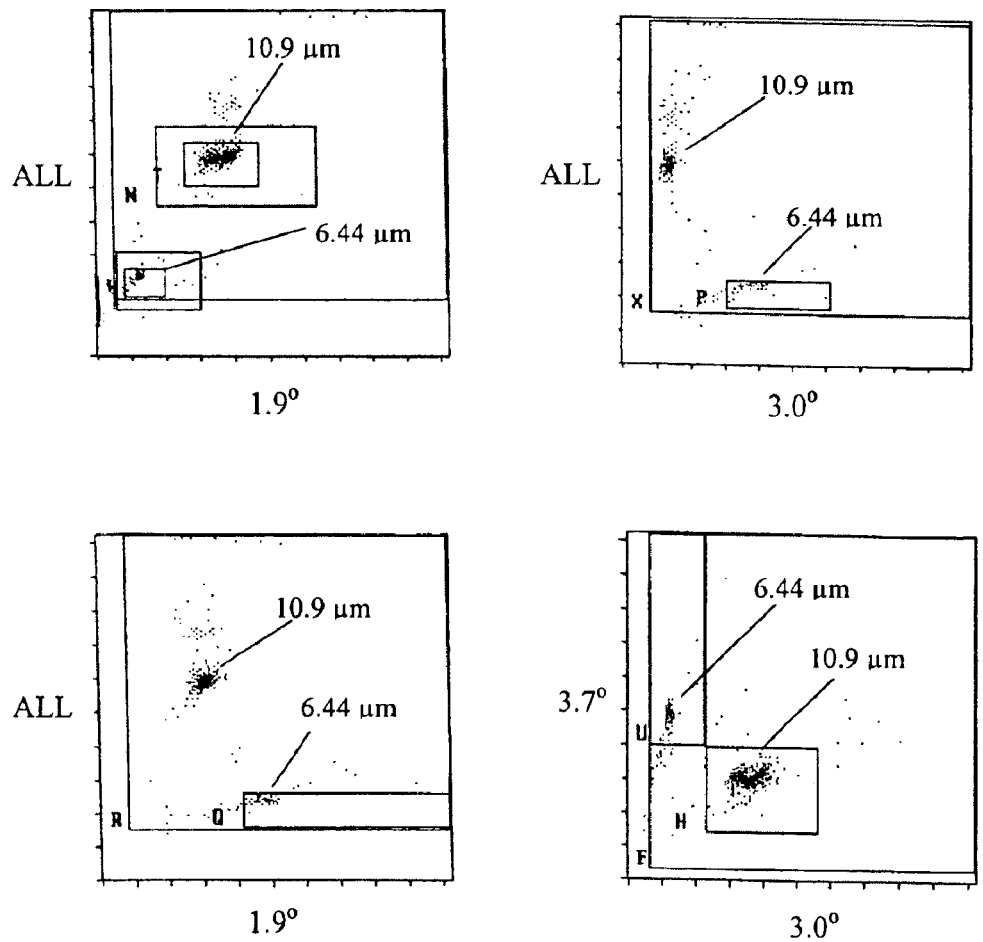
FIG. 4 illustrates the scattergrams of a reference control composition comprising 6.44 μm polystyrene particles and 10.9 μm carboxylated polystyrene particles, suspended in a medium containing stabilized red blood cells and platelets.

Example 3 illustrates incorporation of the above described synthetic spherical particles together with the red blood cell and platelet components into a reference control composition. FIG. 4 shows the scattergrams of the reference control composition comprising 6.44 $\mu$m polystyrene and 10.9 $\mu$m carboxylated polystyrene particles described above, suspended together with stabilized human red blood cells and platelet analogs made of goat red blood cells in an aqueous suspension medium. No analog particle aggregation was observed when the synthetic particles were suspended in the suspension medium in the presence of the stabilized red blood cells and the platelet analogs. Furthermore, no significant optical property change of the individual synthetic particle was observed, although slight shifts in position in the scattergrams were noticed.

Figure 5:
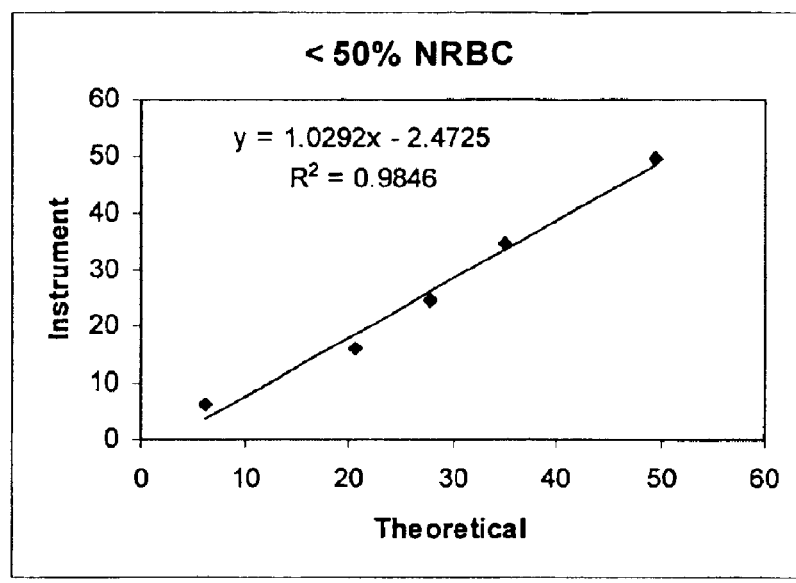
FIG. 5 shows a correlation of the numbers of NRBC per 100 WBC reported by the experimental flow cytometric instrument and the theoretical value in a range of 0 to 50% of NRBC.

The obtained ratio between the NRBC analogs and the white blood cell analogs can be used to report the numbers of NRBC per 100 WBC, which is the same unit used for reporting nucleated red blood cells in a blood sample in clinical laboratories. FIG. 5 shows a correlation of NRBC per 100 WBC reported by the instrument and the theoretical value in a range from 0% to about 50% of NRBC. It is noted that the percentage of NRBC used herein means numbers of NRBC per 100 WBC. As illustrated, the results obtained from the instrument had a linear correlation to the theoretical values.

When the above described reference control composition is used routinely on a hematology analyzer which performs optical measurements of nucleated red blood cells, a deviation of the NRBC and/or WBC analogs in their predetermined positions on a specific scattergram, or a change of count ratio versus a known reference value can indicate an improper instrument operating condition.

In a further embodiment, the present invention provides a reference control system which simulates nucleated red blood cells with different maturities. It is known that human nucleated red blood cells have different sizes depending on their maturity status. In general, the larger the nuclei of nucleated red blood cells the more immature the cells are. Furthermore, within a same clinical blood sample, nucleated red blood cells having different maturities can be observed. Therefore, it is desirable to have a reference control system which further simulates the maturity status of the nucleated red blood cells.

In one embodiment, the reference control system provides a series of reference control compositions, each containing a set of slightly different nucleated red blood cell analogs which simulate the optical properties of human nucleated red blood cells with a specific maturity. As one example, the polystyrene particles having a refractive index of 1.59, but slightly different particle sizes can be used as the NRBC analogs of the reference control system. The reference control system can be packaged in a kit form, wherein each composition is packaged in a separate vial.

The present invention provides the first reference control composition that utilizes synthetic particles to simulate nucleated red blood cells as measured by optical measurements. Using synthetic spherical particles as blood cell analogs has several advantages. The manufacturing process can be much simpler because it does not require a complex NRBC analog preparation process, such as that required when blood cells are used for making the analogs. Because of its chemical inertness, synthetic spherical particles have better stability than cell made analogs.

It has been found that different from prior art teachings, the synthetic particles described above, either the NRBC analog or the WBC analog, have substantially different sizes from the corresponding human nucleated red blood cells or the white blood cells under the lysing condition. More specifically, the mean particle diameter of the NRBC analog particles is from 6.2 $\mu$m to about 6.8 $\mu$m, while the cellular particle diameters of the human nucleated red blood cells under the lysing condition described above is only in a range from about 3.9 $\mu$m to about 4.7 $\mu$m. It is noted that the size measurement of the human nucleated red blood cells under the lysing condition was performed independently by a DC impedance measurement on an experimental hematology instrument as described in U.S. Pat. No. 6,410,330, which is herein incorporated by reference in its entirety. Furthermore, the refractive index of white blood cells is typically about 1.37 to about 1.40. The polystyrene and carboxylated polystyrene particles used as the WBC analogs in the present invention have substantially higher refractive index than that of the native white blood cells to be simulated.

This discovered property is very important because it provides a considerable flexibility in terms of selection of synthetic particles, and substantially reduces the limitations on the particle size for simulating blood cell properties under specific detection conditions, as taught by the prior art.

The following examples are illustrative of the invention and are in no way to be interpreted as limiting the scope of the invention, as defined in the claims.

EXAMPLE 1

An experimental lysing reagent was prepared, which was an aqueous solution containing active components for lysing red blood cells and analysis of nucleated red blood cells: 25.0 g/L of tetradecyltrimethylammonium bromide, 15.0 g/L of Igepal SS-837 (ethoxylated phenol, from Rhone-Poulenc, Cranbury, N.J.), and 4.0 g/L Plurofac A38 prill surfactant (ethoxylated alcohol, from BASF Corp., Florham Park, N.J.).

34 $\mu$l of a whole blood sample was diluted with 850 $\mu$L of an isotonic blood diluent, Isoton® III (Beckman Coulter, Inc., Miami, Fla.), then mixed with 145 $\mu$l of the above described lytic reagent composition. The sample mixture was aspirated by an experimental flow cytometric instrument which is a modified Coulter XL™ flow cytometer (Beckman Coulter, Inc., Miami, Fla.), equipped with an optical detector enabling detection of light scatter signals at various angles including 1.9°±0.5°, 3.0°±0.5°, and 3.7°±0.5°, and axial light loss (0°±0.5°). The sample mixture was drawn through a 50 $\mu$m focused flow cell. Each blood cell was measured, as it passes through the flow cell, by the optical detector.

FIG. 1A shows various obtained scattergrams of a clinical whole blood sample which contained about 5 NRBCs per 100 white blood cells. As shown, the nucleated red blood cells appeared as a distinct cluster in a specific region of ALL vs 1.9°, ALL vs. 3.0°, ALL vs. 3.7°, and 3.7° vs 3.0° scattergrams, respectively.

FIG. 1B shows the corresponding scattergrams of a normal blood sample obtained under the same condition, where no population appeared in the corresponding NRBC regions.

EXAMPLE 2

Two sets of polystyrene particles having a refractive index of 1.59, mean diameters of 6.44 $\mu$m and 7.22 $\mu$m, respectively, were each suspended in an aqueous solution of nonionic surfactant Tween® 20 (Polyoxyethylene sorbitan monolaureate, J T Baker, Phillipsburg, N.J.). Each particle suspension has a particle concentration from about 3.0×10$^3$/$\mu$l to 6.0×10$^3$/$\mu$l. Both sets of the polystyrene particles are the products of Bangs Laboratories, Inc., Fishers, Ind. These particles had a narrow size distribution with a standard deviation of the diameter about 0.07 $\mu$m.

34 $\mu$l of the particle suspension solution was diluted with 850 $\mu$l of Isoton® III, then mixed with 145 $\mu$l of the lytic reagent composition of Example 1. The sample mixture was aspirated, and measured by the experimental flow cytometric instrument described in Example 1.

FIG. 2 shows scattergrams of 6.44 μm polystyrene particles. The particles located in the corresponding NRBC regions of the human blood sample.

FIG. 3 shows scattergrams of 7.22 μm polystyrene particles. The particles located in the corresponding regions where human white blood cells located.

As shown, the 6.44 μm polystyrene particles simulated human nucleated red blood cells, and the 7.22 μm polystyrene particles simulated human white blood cells under the described reaction and detection conditions, respectively.

EXAMPLE 3

Two sets of synthetic particles were each suspended in an aqueous solution of nonionic surfactant Tween® 20 to form two particle suspensions. The first set of particles was polystyrene particles having a mean diameter of 6.44 μm and a refractive index of 1.59. The second set of particles was carboxylated polystyrene particles having a mean diameter of 10.9 μm and a refractive index of 1.60. The 10.9 μm particles were dark blue. Both sets of particles are the products of Bangs Laboratories, Inc., Fishers, Ind.

A reference control composition was prepared by adding a predetermined amount of each particle suspension into an aqueous cell suspension medium (composition provided below) which contained a mixture of stabilized human red blood cells and platelet analogs made of goat red blood cells. The stabilized human red blood cells and the platelet analogs were separately suspended in analog suspension media prior to use. The analog concentrations in the reference control composition were about $1.9 \times 10^6/\mu l$ of stabilized human red blood cells, about $23 \times 10^3/\mu l$ of platelet analogs, about $0.5 \times 10^3/\mu l$ of NRBC analogs (6.44 μm particles), and about $5 \times 10^3/\mu l$ of WBC analogs (10.9 μm particles). Other suitable cell suspension media have been described in the U.S. Pat. Nos. 4,704,364, 5,320,964 and 5,512,485, which are herein incorporated by reference in their entirety.

| Cell Suspension Medium | |
|---|---|
| | Preferred Concentration (g or ml/liter) |
| Propyl paraben | 0.3 to 1.0 g |
| Methyl paraben | 0.5 to 1.0 g |
| Procaine hydrochloride | 0.1 to 0.5 g |
| Deoxycholic acid | 0.1 to 0.9 g |
| Lactose | 10.0 to 50.0 g |
| Actidione | 0.1 to 0.6 g |
| Trisodium citrate dehydrate | 3.0 to 8.0 g |
| Citric acid monohydrate | 0.3 to 0.9 g |
| Sodium dihydrogenphosphate monohydrate | 0.8 to 2.5 mg |
| Phenergan hydrochloride | 0.1 to 1.0 g |
| Colistimethate, sodium | 0.2 to 0.9 g |
| Penicillin G., sodium | $0.5 \times 10^6$ to $3 \times 10^6$ units |
| Kanamycin sulfate | 0.2 to 0.8 g |
| Neomycin sulfate | 0.2 to 1.0 g |
| 5'-AMP | 0.4 to 1.0 g |
| Adenine | 0.2 to 0.8 g |
| Inosine | 0.4 to 1.0 g |
| Dihydrostreptomycin sulfate | 0.2 to 1.0 g |
| Tetracycline hydrochloride | 0.2 to 1.0 g |
| 30% Bovine albumin | 100 to 350 ml |
| Qs to 1 liter with distilled water | |

34 μl of the reference control composition was diluted with 850 μl of Isoton® III, then mixed with 145 μl of the lytic reagent composition of Experiment 1 to lyse the stabilized red blood cells. The sample mixture was aspirated, and measured by the experimental flow cytometric instrument described in Example 1.

FIG. 4 illustrates the scattergrams of the reference control composition. As shown, the NRBC analogs made of 6.44 μm particles appeared in the corresponding NRBC regions of the human blood sample, and the WBC analogs made of 10.9 μm particles appeared in the corresponding NRBC regions of the human blood sample, respectively. The red blood cells and platelet analogs did not show in the scattergrams, as expected for the corresponding cells of the human blood sample under the reaction condition.

EXAMPLE 4

A series of reference control compositions were prepared as described in Example 3, each containing the NRBC analogs made of 6.44 μm polystyrene particles and the WBC analogs made of 10.9 μm carboxylated polystyrene particles described above. The concentration of the WBC analogs was kept constant, and the NRBC analog concentration varied in a range to produce a ratio of the NRBC analogs to the WBC analogs between 0% to about 50% NRBC. Each reference control composition contained about $1.9 \times 10^6/\mu l$ of stabilized human red blood cells and about $23 \times 10^3/\mu l$ of platelet analogs.

Each reference control composition was aspirated and measured on the experimental flow cytometric instrument described in Example 1, following the procedure described in Example 3.

The numbers of NRBC per 100 WBC obtained from the analyses of the scattergrams were plotted against the theoretical values of the NRBC analog concentrations. FIG. 5 shows the obtained correlation curve. As shown, the measured NRBC concentrations (in the numbers of NRBC per 100 WBC) of the reference controls correlates linearly to the theoretical values within the concentration range measured.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents.

We claim:

1. A reference control composition for measurement of nucleated blood cells comprising an amount of synthetic spherical particles having a mean particle diameter ranging from about 6.2 μm to about and a refractive index from about 1.58 to about 1.62 monodispersed aqueous suspension medium and a blood cell component; wherein said synthetic spherical particles have optical properties simulating optical properties of nucleated red blood cells as measured by optical measurements.

2. The reference control composition of claim 1 wherein said blood cell component comprises a white blood cell component.

3. The reference control composition of claim 2 further comprising a red blood cell component and a platelet component.

4. The reference control composition of claim 3 further comprising a reticulocyte component.

5. The reference control composition of claim 1, wherein said synthetic spherical particles simulate said optical properties of nucleated red blood cells having a specific cell maturity.

6. The reference control composition of claim 1, wherein said synthetic spherical particles are polystyrene particles having a refractive index about 1.59.

7. The reference control composition of claim 1, wherein said optical measurements are a low angle light scatter measurement and an axial light loss measurement, or two low angle light scatter measurements.

8. A reference control system for measurement of nucleated blood cells comprising a series of reference control compositions, each of said series of reference control compositions comprising an amount of synthetic spherical particles having a mean particle diameter ranging from about 6.2 μm to about 6.8 μm and a refractive index from about 1.58 to about 1.62 monodispersed in an aqueous suspension medium and a blood cell component; wherein the synthetic spherical particles of said each of said series of reference control compositions have optical properties which simulate optical properties of nucleated red blood cells having a specific cell maturity as measured by optical measurements.

9. The reference control system of claim 8, wherein said blood cell component comprises a white blood cell component.

10. The reference control system of claim 9, wherein each of said series of reference control compositions further comprises a red blood cell component and a platelet component.

11. The reference control system of claim 10, wherein each of said series of reference control compositions further comprises a reticulocyte component.

12. The reference control system of claim 8, wherein said synthetic spherical particles are polystyrene particles having a refractive index about 1.59.

13. The reference control composition of claim 8, wherein said optical measurements are a low angle light scatter measurement and an axial light loss measurement, or two low angle light scatter measurements.

14. A reference control composition for measurement of nucleated blood cells comprising at least two sets of synthetic spherical particles having a mean particle diameter ranging from about 6 μm to about 12 μm and a refractive index from about 1.58 to about 1.62 monodispersed in an aqueous suspension medium and a blood cell component; wherein a first set of said synthetic spherical particles has optical properties simulating optical properties of nucleated red blood cells as measured by optical measurements; and a second set of said synthetic spherical particles has optical properties simulating optical properties of white blood cells as measured by said optical measurements.

15. The reference control composition of claim 14 wherein said blood cell component comprises a red blood cell component and a platelet component.

16. The reference control composition of claim 14, wherein said first set synthetic spherical particles are polystyrene particles having a refractive index of 1.59.

17. The reference control composition of claim 14, wherein said second set synthetic spherical particles are polystyrene particles or carboxylated polystyrene particles.

18. The reference control composition of claim 14, wherein said optical measurements are a low angle light scatter measurement and an axial light loss measurement, or two low angle light scatter measurements.

19. A reference control composition for measurement of nucleated blood cells comprising multiple sets of synthetic spherical particles having a mean particle diameter ranging from about 6 μm to about 12 μm and a refractive index from about 1.58 to about 1.62 monodispersed in an aqueous suspension medium and a blood cell component; wherein a first set of said synthetic spherical particles has optical properties simulating optical properties of nucleated red blood cells as measured by optical measurements, and at least two sets of said synthetic spherical particles have optical properties simulating optical properties of at least two white blood cell subpopulations as measured by said optical measurements.

20. The reference control composition of claim 19 wherein said blood cell componet comprises a red blood cell component and a platelet component.

21. The reference control composition of claim 19, wherein said optical measurements are a low angle light scatter measurement and an axial light loss measurement, or two low angle light scatter measurements.

22. A method of using a reference control composition for measurement of nucleated blood cells comprising the steps of:

(a) providing a reference control composition to a flow cytometric instrument capable of measuring nucleated red blood cells by optical measurements, said reference control composition comprising an amount of one type of synthetic spherical particles having a mean particle diameter ranging from about 6 μm to about 6.8 μm and a refractive index from about 1.58 to about 1.62 monodispersed in an aqueous suspension medium; wherein said synthetic spherical particles have optical properties simulating optical properties of nucleated red blood cells as measured by said optical measurements;

(b) analyzing said reference control composition in a focused flow cell by said optical measurements; and (c) reporting numbers of nucleated red blood cells of said reference control composition.

23. The method of claim 22, where said reference control composition further comprises a white blood cell component in said suspension medium, and said method further comprises analyzing and reporting white blood cells of said reference control composition.

24. The method of claim 23, where said reference control composition further comprises a red blood cell component and a platelet component dispersed in said suspension medium, and said method further comprises analyzing and reporting red blood cells and platelets of said reference control composition.

25. The method of claim 22, wherein said optical measurements are a low angle light scatter measurement and an axial light loss measurement.

26. The method of claim 22, wherein said optical measurements are two low angle light scatter measurements.

27. A method of using a reference control composition for measurement of nucleated blood cells comprising the steps of:

(a) providing a reference control composition to a flow cytometric instrument capable of measuring nucleated red blood cells by optical measurements, said reference control composition comprising multiple sets of synthetic spherical particles having a mean particle diameter ranging from about 6 μm to about 12 μm and a refractive index from about 1.58 to about 1.62 monodispersed in an aqueous suspension medium; wherein a first set of said synthetic spherical particles has optical properties simulating optical properties of nucleated red blood cells as measured by said optical measurements, and a second set of said synthetic spherical particles has optical properties simulating optical properties of white blood cell as measured by said optical measurements;

(b) analyzing said reference control composition in a focused flow cell by said optical measurements; and (c) differentiating said first set and said second set of said synthetic spherical particles, and reporting numbers of nucleated red blood cells and numbers of white blood cells of said reference control composition.

28. The method of claim 27, where said reference control composition further comprises a red blood cell component and a platelet component dispersed in said suspension medium, and said method further comprises analyzing and reporting red blood cells and platelets of said reference control composition.

29. The method of claim 27, wherein said optical measurements are a low angle light scatter measurement and an axial light loss measurement.

30. The method of claim 27, wherein said optical measurements are two low angle light scatter measurements.

* * * * *

UNITED STATES PATENT AND TRADEMARK OFFICE
CERTIFICATE OF CORRECTION

| | |
|---|---|
| PATENT NO. | : 6,962,817 B2 |
| APPLICATION NO. | : 10/955104 |
| DATED | : November 8, 2005 |
| INVENTOR(S) | : Yi Li et al. |

It is certified that error appears in the above-identified patent and that said Letters Patent is hereby corrected as shown below:

Column 10, line 50, after "about 6.2 µm to about" insert -- 6.8µm--

Column 10, line 51, after "monodispersed" insert -- in an --

Signed and Sealed this

Twenty-ninth Day of August, 2006

JON W. DUDAS
*Director of the United States Patent and Trademark Office*